(12) United States Patent
Okazoe et al.

(10) Patent No.: US 6,833,477 B2
(45) Date of Patent: Dec. 21, 2004

(54) PROCESS FOR PRODUCING A VIC-DICHLORO ACID FLUORIDE

(75) Inventors: Takashi Okazoe, Kanagawa (JP); Kunio Watanabe, Kanagawa (JP); Masahiro Ito, Kanagawa (JP); Daisuke Shirakawa, Kanagawa (JP); Shin Tatematsu, Kanagawa (JP)

(73) Assignee: Asahi Glass Company, Limited, Tokyo (JP)

(*) Notice: Subject to any disclaimer, the term of this patent is extended or adjusted under 35 U.S.C. 154(b) by 0 days.

(21) Appl. No.: 10/084,506

(22) Filed: Feb. 28, 2002

(65) Prior Publication Data

US 2002/0107358 A1 Aug. 8, 2002

Related U.S. Application Data

(63) Continuation of application No. PCT/JP00/05888, filed on Aug. 30, 2000.

(30) Foreign Application Priority Data

Aug. 31, 1999 (JP) .............................. 11-246154
Jul. 12, 2000 (JP) ...................... 2000-211722

(51) Int. Cl.$^7$ .............................................. C07C 51/09
(52) U.S. Cl. ...................... 562/849; 562/863
(58) Field of Search ................................ 562/849, 863

(56) References Cited

U.S. PATENT DOCUMENTS

| 3,900,372 A | 8/1975 | Childs et al. |
| 5,093,432 A | 3/1992 | Bierschenk et al. |
| 5,322,903 A | 6/1994 | Bierschenk et al. ...... 525/331.6 |
| 5,322,904 A | 6/1994 | Bierschenk et al. ...... 325/331.6 |
| 5,332,790 A | 7/1994 | Bierschenk et al. ...... 525/331.6 |
| 5,461,117 A | 10/1995 | Bierschenk et al. ...... 525/331.6 |
| 5,466,877 A | 11/1995 | Moore .................... 562/852 |
| 5,571,870 A | 11/1996 | Bierschenk et al. ...... 525/331.6 |
| 5,674,949 A | 10/1997 | Bierschenk et al. ...... 525/331.6 |
| 5,753,776 A | 5/1998 | Bierschenk et al. ...... 525/331.6 |
| 6,255,535 B1 | 7/2001 | Schulz et al. ............ 568/615 |

FOREIGN PATENT DOCUMENTS

JP  02311438  * 12/1990  ........... C07C/43/17

OTHER PUBLICATIONS

Murata et al., The Thermal Decomposition of Perfluoroesters, J. Am. Chem. Soc., vol. 120, No. 28, Jul. 1998, pp. 7117–7118.*

U.S. Appl. No. 10/833,048, filed Apr. 28, 2004, Okazoe et al.
U.S. Appl. No. 10/084,506, filed Apr. 28, 2002, Okazoe et al.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

The process for producing a vic-dichloro acid fluoride compound in a short process and in good yield from the starting material which is inexpensive and readily available is provided. $(R^{H1}-E_{H1}-)CR^{H2}R^{H3}CH_2-OCOR^{HB}$ (I) is fluorinated in a liquid phase to form $(CF_2ClCFCl-EF^{F1}-)CR^{F2}R^{F3}CF_2-OCOR^{FB}$ (II), and then, an ester bond of the compound (II) is decomposed to form $(CF_2ClCFCl-E^{F1}-)CR^{F2}R^{F3}COF$(III) or the compound (III) and $FCOR^{FB}$ (IV).

25 Claims, No Drawings

PROCESS FOR PRODUCING A VIC-DICHLORO ACID FLUORIDE

This application is a Continuation of International application No. PCT/JP00/05888 Filed on: Aug. 30, 2000, pending.

TECHNICAL FIELD

The present invention relates to new process for producing an acid fluoride compound having a vic-dichloro structure, which is useful for an intermediate compound for producing a starting monomer of a fluorinated resin.

BACKGROUND ART

A compound having a perfluoroalkyl chain having a vic-dichloro structure (a structure wherein one chlorine atom is bonded to each of two adjacent carbons) at its terminal and a fluorocarbonyl group (—COF) is useful as an intermediate compound for producing a material monomer of a fluorinated resin, or a fluororesin. For example, a compound having —$CF_2ClCFCl$ can be reacted with zinc and then dechlorinated to form an acid fluoride compound having a perfluorovinyl group ($CF_2$=CF—). A perfluorovinyl group of such a compound is a polymerizable group and thus various fluorinated resins can be produced by polymerization of such a compound. The resulting fluorinated resins are useful resins excellent in heat resistance and chemical resistance.

Among the above-mentioned fluorinated resins, for example, a homopolymer of perfluoro(3-butenyl vinyl ether) [$CF_2$=$CFCF_2CF_2OCF$=$CF_2$] is used in various fields as a transparent fluorinated resin. A monomer of such a fluorinated resin, perfluoro(3-butenyl vinyl ether) is conventionally prepared by the following manufacturing route.

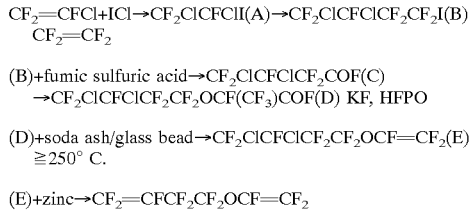

Namely, $CF_2$=CFCl is reacted with iodine chloride to form the compound (A), which is reacted with tetrafluoroethylene to form the compound (B), which is reacted with fuming sulfuric acid to form the compound (C). Further, the compound (C) is reacted with hexafluoropropylene oxide (HFPO) in the presence of an alkali fluoride such as KF etc. to form the compound (D), which is heated at least 250° C. in the presence of soda ash or a glass bead to form the compound (E), which is reacted with zinc to prepare perfluoro(3-butenyl vinyl ether) through dechlorination.

Such a conventional process for producing perfluoro(3-butenyl vinyl ether) etc. has had a drawback such that an isomer, $CF_2ICFCl_2$, is produced as well as the compound (A) in a step of producing the compound (A). The amount of the isomer is difficult to control. Further, the conventional production process has been economically disadvantageous since it includes a lot of reaction steps and its starting material is expensive. In addition, there have been difficult problems such as corrosion of the apparatus and the handling of the reagents resulted from using iodine chloride and fuming sulfuric acid etc.

On the other hand, as a method of fluorinating all of C—H bonds to C—F in a hydrocarbon compound, there have been known a direct fluorinating methods using elemental fluorine (hereafter, a direct fluorination), and a fluorinating method using a product prepared by electrolyzing hydrogen fluoride in an electrolysis cell (so called as an electrochemical fluorination). As a direct fluorination, there have been known a fluorinating method in a gas phase (hereinafter, gas phase reaction) and a fluorinating method in a liquid phase (hereinafter, liquid phase reaction).

A process for producing an acid fluoride compound has also been known by way of a thermal decomposition of a perfluorinated ester compound having at least 16 carbon numbers. It has been described that such a acid fluoride compound can be prepared by using a hydrocarbon ester compound having a corresponding carbon skeleton as its starting material and by directly fluorinating it using elemental fluorine in a liquid phase (J. Am. Chem. Soc., 120.7117 (1998)).

It has also been proposed that a process for reacting a perfluoroalkyl ester containing no chlorine atom in the presence of a nucleophile and a solvent to form a perfluoro acid fluoride (U.S. Pat. No. 5,466,877).

However, it has not been conventionally conceived nor proposed that an acid fluoride having a vic-dichloro structure such as perfluoro(3,4-dichlorobutyl vinyl ether, which is a precursor to perfluoro(3-butenyl vinyl ether), could be produced by the direct fluorinating method or the electrochemical fluorination reaction mentioned above.

The object of the present invention is to provide a process for producing an acid fluoride (III) having a vic-dichloro structure such as perfluoro(3,4-dichlorobutyl vinyl ether, which is a precursor to perfluoro(3-butenyl vinyl ether), in a short process from raw material available at a low cost. Conventionally, such a process was economically disadvantageous that it requires many reaction steps and high cost of the starting material and includes difficult problems such as corrosion of the apparatus and handling of the reagents resulted from using iodine chloride and fuming sulfuric acid etc.

THE DISCLOSURE OF THE INVENTION

The present invention provides a process for producing a vic-dichloro acid fluoride compound comprising fluorinating the following compound (I) in a liquid phase to form the following compound (II), and dessociating an ester bond of the compound (II) to form the following compound (III), or the following compound (III) and the following compound (IV):

$$(R^{H1}-E^{H1}-)CR^{H2}R^{H3}CH_2-OCOR^{HB} \quad (I)$$

$$(CF_2ClCFCl-E^{F1}-)CR^{F2}R^{F3}CF_2-OCOR^{FB} \quad (II)$$

$$(CF_2ClCFCl-E^{F1}-)CR^{F2}R^{F3}COF \quad (III)$$

$$FCOR^{FB} \quad (IV)$$

wherein, $R^{H1}$: $CX^1X^2ClCX^3Cl$— or $CClX^4$=CCl—, wherein each of $X^1$-$X^4$ is independently a hydrogen atom or a fluorine atom, $R^{H2}$, $R^{H3}$: each independently is a hydrogen atom, a fluorine atom, a monovalent saturated hydrocarbon group, a halogeno monovalent saturated hydrocarbon group, a hetero atom-containing monovalent saturated hydrocarbon group or a halogeno (hetero atom-containing monovalent saturated hydrocarbon) group, $E^{H1}$: a bivalent connecting group or a single bond, $E^{F1}$: a group corresponding to $E^{H1}$, and when $E^{H1}$ is a single bond, $E^{F1}$ is a single bond, and when $E^{H1}$ is a bivalent connecting group having one or more hydrogen atoms, $E^{F1}$ is a group corresponding to $E^{H1}$ wherein at least one hydrogen atom is fluorinated, and when $E^{H1}$ is a bivalent connecting group having no hydrogen atom, $E^{F1}$ is the same group as $E^{H1}$, $R^{HB}$: a monovalent saturated hydrocarbon group, a halogeno monovalent saturated hydrocarbon group, a hetero atom-containing monovalent saturated hydrocarbon group or a halogeno(hetero atom-containing monovalent saturated hydrocarbon) group, $R^{F2}$, $R^{F3}$, $R^{FB}$: $R^{F2}$ is a fluorinated $R^{H2}$ group, $R^{F3}$ is a fluorinated $R^{H3}$ group, $R^{FB}$ is a fluorinated $R^{HB}$ group, provided that, when one or more hydrogen atom are present in $R^{H2}$, $R^{H3}$ or $R^{HB}$, $R^{F2}$, $R^{F3}$ or $R^{FB}$ is a group corresponding to $R^{H2}$, $R^{H3}$ and $R^{HB}$, respectively, wherein at least one hydrogen is fluorinated, and when no hydrogen atom is present in $R^{H2}$, $R^{H3}$ or $R^{HB}$. $R^{F2}$, $R^{F3}$ or $R^{FB}$ is a group corresponding to $R^{H2}$, $R^{H3}$ or $R^{HB}$ respectively.

According to the present invention, an acid fluoride (III) having a vic-dichloro structure can be produced in a short process and in a good yield from the compound (I) available at a low cost, as described in detail later.

The process of the present invention does not include difficult problems such as corrosion of the apparatus and handling of the reagents since iodine chloride and fuming sulfuric acid etc. are not employed.

Further, a continuous process for producing an acid fluoride (III) having a vic-dichloro structure is also provided, wherein a compound (IV) obtained together with an acid fluoride (III) is recycled into the starting material producing step.

Moreover, new chemical compounds are provided by way of the reaction steps of the present invention.

Best Mode For Carrying Out the Invention

[Explanation of the Terms Used in the Invention]

In the present specification, a monovalent saturated hydrocarbon group may be a straight chain structure, a branched structure, a cyclic structure (that is, a cycloalkyl group) means organic or a structure having a partially cyclic structure. The carbon number of the monovalent saturated hydrocarbon group is preferably from 1 to 20, particularly preferably from 1 to 10.

In the present specification, a halogen atom may be a fluorine atom, a chlorine atom, a bromine atom or an iodine atom, and a fluorine atom, a chlorine atom or a bromine atom is preferred.

Further, in the present specification, "halogeno" means that at least one hydrogen atom in a group is substituted with at least one halogen atom selected from a fluorine atom, a chlorine atom, a bromine atom and an iodine atom. In the group of a halogeno group, a hydrogen atom may or may not be present. "fluoro" etc. means in the same manner.

The "partially halogeno" means that a hydrogen atom which is not substituted by a halogen atom is present in the group of a halogeno group. "partially fluoro" and "perfluoro", etc. mean in the same manner.

In the present specification, the halogeno monovalent hydrocarbon group may be a group having at least one hydrogen atom in the above-mentioned monovalent saturated hydrocarbon group substituted by a halogen atom. The halogen atom in the halogeno monovalent hydrocarbon group is preferably a fluorine atom, a chlorine atom or a bromine atom. As such a halogen atom in the halogeno monovalent hydrocarbon group, a fluorine atom alone or a fluorine and a halogen atom other than a fluorine atom is particularly preferred. As specific examples of these groups, the groups disclosed in the examples of the following compounds may be mentioned.

As the hetero atom-containing monovalent saturated hydrocarbon group in the present specification, a hetero atom or a group having a hetero atom which undergo no change by the fluorination reaction in the above-mentioned monovalent saturated hydrocarbon group may be mentioned. Particularly preferred is a group having a bivalent hetero atom or a bivalent hetero atom group which undergo no change by the fluorination reaction in the above-mentioned monovalent saturated hydrocarbon group.

As the bivalent hetero atom which undergoes no change by the fluorination reaction is preferably an etheric oxygen atom, and the bivalent hetero atom group which undergoes no change by the fluorination reaction may be —C—C(=O)—C—, —C—SO$_2$—C—, etc.

The hetero atom-containing monovalent saturated hydrocarbon group is preferably an alkyl group containing an etheric oxygen atom, a group having an etheric oxygen atom inserted between carbon-carbon atoms in a cycloalkyl group, or a monovalent saturated hydrocarbon group having an etheric oxygen atom inserted between carbon—carbon atoms in a cycloalkyl group.

Further, the halogeno (hetero atom-containing monovalent saturated hydrocarbon group) may be a group having at least one hydrogen atom in the above-mentioned hetero atom-containing monovalent saturated hydrocarbon group substituted by a halogen atom, and a halogeno(alkoxyalkyl) group or a halogenoalkoxyl group may be mentioned.

[The Explanation of the Compound (I)]

In the compound (I), $R^{H1}$ is $CX^1X^2ClCX^3Cl$— or $CClX^4=CCl$— (provided that $X^1$–$X^4$ is independently a hydrogen atom or a fluorine atom), and all of $X^1$–$X^4$ is preferably a hydrogen atom from the view point of the availability of the starting material and the economical reason in the process of the present invention.

$E^{H1}$ is a single bond wherein $R^{H1}$ and a carbon atom bonding $R^{H2}$ and $R^{H3}$ are directly bonded. When $E^{H1}$ is a bivalent bonding group, a bivalent saturated hydrocarbon group, a halogeno bivalent saturated hydrocarbon group, a bivalent (hetero atom-containing saturated hydrocarbon group or a halogeno bivalent (hetero atom-containing saturated hydrocarbon group is preferred. The bivalent bonding group may be of a straight chain structure, a branched chain structure or a structure containing a cyclic structure.

The structures of $R^{H2}$ and $R^{H3}$ may be properly modified depending on the structure of the objective compound and is preferably a hydrogen atom, an alkyl group, a halogeno alkyl group, a hetero atom-containing alkyl group or a hetero atom-containing halogeno alkyl group because of their availability. Since a fluorine atom can be introduced into $R^{H2}$ and $R^{H3}$ by the fluorination reaction described later, a group containing a halogen atom other than a fluorine atom is preferred from the economical reason, when $R^{H2}$ and $R^{H3}$ are halogeno groups.

$E^{H1}$, $R^{H2}$ and $R^{H3}$ are properly selected from the structure corresponding to the objective compound (III), respectively and are preferably a group containing no fluorine atom from the view point of availability and the economical reason etc. about the production process. Further, $E^{H1}$ is preferably an alkylene group or a hetero atom-containing alkylene group, and $R^{H2}$ and $R^{H3}$ are preferably hydrogen atom or a hetero atom-containing alkyl group.

The structure of $R^{HB}$ is preferably adjusted so that the compound (I) will be readily soluble in a liquid phase to be used at the time of fluorination. $R^{HB}$ is preferably a halogeno alkyl group or a halogeno (hetero atom-containing alkyl) group, and is more preferably a group containing a fluorine atom as an essential atom, among which a perfluoro alkyl group, a perfluoro(partially chlorinated alkyl) group, a perfluoro(hetero atom-containing alkyl) group or a perfluoro (partially chlorinated (hetero atom-containing alkyl) group is particularly preferred. $R^{HB}$ is particularly preferably a group containing a fluorine atom as an essential atom, since the compound (I) is satisfactorily soluble in a liquid phase, and the fluorination of the compound (I) can be carried out in a homogeneous phase at the time of the fluorination of the compound (I) in a liquid phase.

Further, the fluorine content in the compound (I) (the proportion of the fluorine atoms in the molecule) is preferably modified depending on the kind of the liquid phase to be used in the fluorination. Usually, the lower limit of the fluorine content (the ratio of the fluorine atoms to the molecular weight of the compound) is preferably 10% by mass, particularly preferably 30% by mass and the upper limit is preferably 86% by mass, particularly preferably 80% by mass. The molecular weight of the compound (I) is preferably from 300 to 1000, whereby the reaction in a gas phase can be suppressed and the reaction in a liquid phase can be smoothly carried out at the time of fluorination reaction. If the molecular weight is too small, the compound (I) tends to be readily volatile, and it is likely that a decomposition reaction may take place in a gas phase during the fluorination reaction in a liquid phase. On the other hand, if the molecular weight is too large, purification of the compound (I) tends to be difficult.

As the compound (I), various known compounds and new compounds in the following may be mentioned.

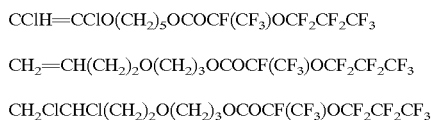

[Conversion from Compound (I) to Compound (II)]

In the present invention, the compound (I) is fluorinated in a liquid phase. As the fluorinating method in a liquid phase, a method of fluorinating the compound (I) with elemental fluorine in a solvent (fluorination method-1) or an electrochemical fluorination (fluorination method-2) may be mentioned, and fluorination method-1 is preferred among them.

When the fluorination is carried out by fluorination method-2, it is preferred that the compound (I) is dissolved in anhydrous hydrofluoric acid to obtain a solution, and the solution is electrolyzed in an electrolytic cell to fluorinate the compound(I) to form the compound(II).

When the fluorination is carried out by fluorination method-1, the compound (I) and fluorine gas are reacted in a solvent (hereinafter referred to solvent-1) to form the compound(II). As the fluorine gas, fluorine gas of 100% or fluorine gas diluted with an inert gas may be used. As the inert gas, nitrogen gas and helium gas are preferred, and nitrogen gas is particularly preferred from an economical reason. The amount of fluorine gas in the mixed gas of the inert gas and fluorine gas is preferably at least 5 vol. % from the view point of the efficiency and from 5 to 30 vol. % is particularly preferred since an abstraction of the chlorine atom and a migration of the chlorine atom can be prevented.

Solvent-1 to be used for fluorination method-1 is preferably a solvent which contains no C—H bond and which necessarily contains a C—F bond. Further, it is preferred to use a perfluoroalkane or an organic solvent obtained by perfluorinating a known organic solvent having at least one atom selected from a chlorine atom, a nitrogen atom and an oxygen atom in its structure. Further, as solvent-1, it is preferred to employ a solvent which provides a high solubility to the compound (I), and it is particularly preferred to employ a solvent which is capable of dissolving at least 1% by mass of the compound(I), particularly a solvent which is capable of dissolving at least 5% by mass.

Examples of solvent-1 may be the compound (II), the compound (III), the compound (IV), perfluoroalkanes (such as FC-72), perfluoroethers (such as FC-75, FC-77), perfluoropolyethers (such as trade names: KRYTOX, FOMBLIN, GALDENE and DEMNUM), chlorofluorocarbons (trade name: FLONLUBE), chlorofluropolyethers, perfluoroalkylamines (such as perfluorotrialkylamine), and an inert fluid (trade name: FLUORINERT). Among others, a perflurotrialkylamine or the compound (II) is preferred as solvent-1. Particularly when the compound (II) is employed, there will be a merit that work-up after the reaction will be easy. The amount of solvent-1 is preferably at least 5 times by mass, particularly from 10 to 100 times by mass, relative to the compound (I).

The reaction type of the fluorination reaction of fluorination method-1 is preferably a batch system or a continuous system. Especially from the view point of the reaction yield and selectivity, a continuous system which will be described hereinafter is preferred, and among them, a continuous system (2) is particularly preferred. Further, fluorine gas may be the one diluted with an inert gas such as nitrogen gas in any case wherein the reaction is carried out by a batch system or by a continuous system.

[Continuous system (1)] Into a reactor, the compound (I) and solvent-1 are charged, and stirring is initiated. This is a method of reacting at a predetermined reaction temperature and reaction pressure while supplying fluorine gas continuously.

[Continuous system (2)] Into a reactor, solvent-1 is charged, and stirring is initiated. This is a method of supplying the compound (I), solvent-1 and fluorine gas at a predetermined reaction temperature and reaction pressure in a predetermined molar ratio continuously and simultaneously.

In the continuous system (2), the compound (I) may be or not diluted with solvent-1, when the compound(I) is supplied. Further, in the continuous system (2), when the compound (I) is diluted with a solvent, it is preferred to adjust the amount of solvent-1 to at least 5 times by mass, particularly preferably at least 10 times by mass, relative to the compound (I).

When the reaction is carried out by a batch system, it is preferred to charge fluorine gas so that the amount of fluorine atoms is always excess equivalent, relative to hydrogen atoms in the compound (I), and it is particularly preferred that fluorine gas is used so that it becomes at least 1.5 times by equivalent(at least 1.5 times by mol), relative to hydrogen atoms in the compound (I), from the view point of selectivity. Further, when the reaction is carried out by a continuous system, it is preferred to continuously supply fluorine gas so that the amount of fluorine atoms will be excess equivalent, relative to hydrogen atoms in the compound (I), and it is particularly preferred to continuously supply fluorine gas so that it becomes at least 1.5 times by equivalent (at least 1.5 times by mol), relative to hydrogen atoms in the compound (I), from the view point of the selectivity.

The reaction temperature for the fluorination reaction by fluorination method-1 may be varied depending on the structure of $E^{H1}$, and it is preferably at least −60° C. and at most the boiling point of the compound (I). From the view point of the reaction yield, the selectivity and efficiency for industrial operation, it is particularly preferably from −50 to +100° C., and it is especially preferably from −20 to +50° C. to prevent abstraction and migration of a chlorine atom. The reaction pressure of the fluorination reaction is not particularly limited, and it is particularly preferably from atmospheric pressure to 2 MPa (gage pressure, the same applies to hereinafter) from the viewpoint of the yield, selectivity and efficiency for industrial operation.

Further, in order to let the fluorination method-1 proceed efficiently, it is preferred to add a C—H bond-containing compound to the reaction system or to carry out under irradiation of ultraviolet ray. For example, it is preferred to add a C—H bond-containing compound to the reaction system or to irradiating ultraviolet ray at a later stage of the fluorination reaction. In this way, hydrogen atoms which is usually difficult to fluorinate can be efficiently fluorinated, and the reaction rate can be remarkably improved. The time for ultraviolet irradiation is preferably from 0.1 to 3 hours.

The C—H bond-containing compound is an organic compound other than the compound (I), and an aromatic hydrocarbon is particularly preferred. Especially, for example, benzene or toluene is preferred. The amount of such a C—H bond-containing compound is preferably from 0.1 to 10 mol %, particularly from 0.1 to 5 mol %, relative to hydrogen atoms in the compound (I).

It is preferred to add the C—H bond-containing compound to the reaction system in such a state where elemental fluorine is present. Further, when the C—H bond-containing compound is added, it is preferred to pressurize the reaction system. The pressure during the pressurizing is preferably 0.01 to 5 MPa

[The Explanation of the Compound (II)]

In the fluorination reaction of the compound (I), the compound (II) is formed. Hydrogen atoms of $R^{H1}$ in the compound (II) will be substituted by fluorine atoms in the fluorination reaction, and when $R^{H1}$ is CClX$^4$=CCl—, it will become CF$_2$ClCFCl— since fluorine atoms are added to the double bond moiety.

If $E^{H1}$ is a single bond, $E^{F1}$ will be a single bond, and if $E^{H1}$ is a bivalent connecting group having no hydrogen atom, $E^{F1}$ will be the same group as the bivalent group, and if $E^{H1}$ is a bivalent connecting group having one or more hydrogen atoms, $E^{F1}$ will be the group wherein at least one hydrogen atoms is fluorinated. For example, if $E^{H1}$ is a perhalogeno group, $E^{H1}$ and $E^{F1}$ are the same. If $E^{H1}$ is an alkylene group or a group wherein an etheric oxygen atom is inserted between the carbon-carbon bond of an alkylene group, $E^{F1}$ will be the group wherein at least one hydrogen atom in these groups is substituted by fluorine atom. $E^{F1}$ is preferably a perfluoroalkylene group or a perfluoro(hetero atom-containing )alkylene group.

Each of $R^{F2}$ and $R^{F3}$ is preferably independently a fluorine atom, a partially halogeno or perhalogeno (monovalent saturated hydrocarbon)group, a partially halogeno or perhalogeno(hetero atom-containing monovalent saturated hydrocarbon)group. If a hydrogen atom is not present in $R^{H2}$ and $R^{H3}$, $R^{F2}$ and $R^{F3}$ are the same as $R^{H2}$ and $R^{H3}$, respectively, since $R^{H2}$ and $R^{H3}$ are not influenced by the fluorination in this case. If $R^{H2}$ and $R^{H3}$ contain a hydrogen atom (for example, each of $R^{H2}$ and $R^{H3}$ is a partially fluoro monovalent saturated hydrocarbon) group), each of $R^{F2}$ and $R^{F3}$ is the group, respectively, wherein at least one hydrogen atom in the group is fluorinated, and is preferably a perfluoro monovalent saturated hydrocarbon group. Further, if each of $R^{H2}$ and $R^{H3}$ is a partially chloro monovalent saturated hydrocarbon group, each of $R^{F2}$ and $R^{F3}$ is a fluoro (partially chloro monovalent saturated hydrocarbon group), respectively, wherein at least one hydrogen atom in the group is fluorinated, and are particularly preferably a perfluoro(partially chloroalkyl) group.

$R^{F2}$ and $R^{F3}$ are preferably fluorine atom, a perfluoro monovalent saturated hydrocarbon group or a perfluoroalkoxyl group.

$R^{FB}$ is a group corresponding to $R^{HB}$, and $R^{FB}$ will be the same as $R^{HB}$, when $R^{HB}$ is a halogeno group. When $R^{HB}$ is a hydrogen-containing group, $R^{FB}$ will be a group wherein the hydrogen in the group is fluorinated. $R^{FB}$ is preferably a perfluoroalkyl group or a perfluoro(alkoxy alkyl)group.

In the liquid-phase fluorination reaction of the compound (I), HF will be formed as a by-product. To remove HF formed as a by-product, it is preferred to incorporate an HF scavenger in the reaction system or to contact the outlet gas with an HF scavenger at the gas outlet of the reactor. As an HF scavenger, a base such as an alkali metal fluoride (for example, sodium fluoride, etc.) is preferred, and may be incorporated in the reaction system. The HF scavenger is preferably an alkali metal fluoride, particularly preferably NaF.

When the HF scavenger is incorporated in the reaction system, the amount is preferably from 1 to 20 mol times, more preferably from 1 to 5 mol times, relative to the total amount of hydrogen atoms contained in the compound (I). In a case where the HF scavenger is disposed at the outlet of the reactor, it is preferred to arrange (1) a condenser (preferably maintained at a temperature of from 10° C. to room temperature, particularly preferably at about 20° C.), (2) a packed layer of a HF scavenger such as a NaF pellet and (3) a condenser (preferably maintained at a temperature of from −78° C. to +10° C., more preferably from −30° C. to 0° C.) in a series in the order of (1)-(2)-(3). Further, a liquid-returning line may be installed to return the condensed liquid from the condenser of (3) to the reactor.

The crude product containing the compound (II) obtained by the fluorination reaction may be employed in the next step as it is, or may be purified to a high purity. The purification method may, for example, be a method of distilling the crude product under atmospheric pressure or reduced pressure.

[Conversion from Compound (II) to Compound (III)/Compound (IV)]

Next, in the present invention, the compound (III) and/or the compound (IV) are obtained by dissociation of an ester bond of the compound (II). The objective compound by the production method of the present invention is the compound (III), the compound (IV) or both of the compound (III) and the compound (IV).

The reaction to dissociate the ester bond of the compound (II) is a reaction to form two —COF groups by breaking —CF$_2$OCO—. Such a reaction is preferably carried out by a thermal decomposition reaction or a decomposition reaction which is carried out in the presence of a nucleophile or an electrophile.

The thermal decomposition reaction can be conducted by heating the compound (II). The reaction type of the thermal decomposition reaction is preferably selected by the boiling point and the stability of the compound (II). For example, if the compound (II) which is readily vaporized, will be thermally decomposed. A gas phase thermal decomposition method may be employed in which it is continuously decomposed in a gas phase, and the outlet gas containing the obtained compound (III) is condensed and recovered.

The reaction temperature of the gas phase thermal decomposition method is preferably from 50 to 350° C., particularly preferably from 50 to 300° C., especially preferably from 150 to 250° C. Further, an inert gas which is not concerned directly with the reaction, may be present in the reaction system. As such a inert gas, nitrogen or carbon dioxide may, for example, be mentioned. It is preferred to add an inert gas in an amount of from 0.01 to 50 vol % relative to the compound (II). If the amount of the inert gas is large, the recovery of the product may sometimes decrease.

On the other hand, in a case where the compound (II) is a compound which is hardly vaporized, it is preferred to employ a liquid phase thermal decomposition method wherein it is heated in a liquid state in the reactor. The reaction pressure in this case is not limited. In an usual case, the product obtained from the ester decomposition is of a lower boiling point, and it is preferred to carry out the reaction by using a reactor equipped with a distillation column whereby the product having a low boiling is continuously withdrawn. Otherwise, it may be a method wherein after completion of the heating, the product is withdrawn all together from the reactor. The reaction temperature for the liquid phase thermal decomposition method is preferably from 50 to 300° C., particularly preferably from 100 to 250° C.

When the thermal decomposition is carried out by the liquid phase thermal decomposition method, the decomposition may be conducted in the absence of a solvent or in the present of a solvent (hereinafter referred to as solvent-2). Solvent-2 is not particularly limited so long as it is not reactive with the compound (II), and it is miscible with the compound (II) and is not reactive with the product. Further, as solvent-2, it is preferred to select one which is readily separable at the time of purification of the product. A specific example of solvent-2 is preferably an inert solvent such as perfluorotrialkylamine or perfluorodecalim, or a chlorotrifluorocarbon, particularly preferably chlorotrifluoroethylene oligomer having a high boiling point (for example, trade name: FLONLUBE). The amount of solvent-2 is preferably from 10 to 1000% by mass, relative to the compound (II).

Further, in a case where the compound (II) is decomposed by reacting a nucleophile or an electrophile in a liquid phase, such a reaction may be carried out in the absence of a solvent or in the presence of a solvent (hereinafter referred to as solvent-3). Solvent-3 is preferably the same as solvent-2. The nucleophile is preferably a fluoride anion (F$^-$), particularly a fluoride anion derived from an alkali metal fluoride. The alkali metal fluoride is preferably NaF, NaHF$_2$, KF or CsF. Among them, NaF is particularly preferred from the viewpoint of economical efficiency.

When the nucleophile such as (F$^-$) is employed, F$^-$ is nucleophilically added to a carbonyl group present in the ester bond of the compound (II), whereby $CF_2ClCFClE^{F1}CR^{F2}R^{F3}CF_2O^-$ will be detached, and an acid fluoride [the compound (IV)] will be formed. From $CF_2ClCFClE^{F1}CR^{F2}R^{F3}CF_2O^-$, F$^-$ will further be detached to form an acid fluoride [the compound (III)]. The detached F$^-$ will react with another molecule of the compound (II) in the same manner. Accordingly, the nucleophile to be used at the initial stage of the reaction may be in a catalytic amount or may be used excessively. Namely, the amount of the nucleophile such as F$^-$ is preferably from 1 to 500 mol %, particularly preferably from 1 to 100 mol %, especially preferably from 5 to 50 mol %, relative to the compound (II). The lower limit of the reaction temperature is preferably −30° C., and the upper limit is preferably the boiling point of solvent-3 or the compound (II). The reaction temperature is usually particularly preferably from −20° C. to 250° C. This method is also preferably carried out by using a reactor equipped with a distillation column.

As the compound (II), the following new compounds may be mentioned. The following compounds can be led to the corresponding vic-dichloro acid fluoride compounds by the reaction which will be described in the examples.

$CClF_2CClFO(CF_2)_5OCOCF(CF_3)OCF_2CF_2CF_3$

$CF_2ClCFCl(CF_2)_2O(CF_2)_3OCOCF(CF_3)OCF_2CF_2CF_3$

It is preferred to carry out the decomposition reaction of the ester bond in the presence of NaF. The thermal decomposition reaction can be conducted at low temperature by carrying out the decomposition in the presence of NaF, whereby the decomposition of the compound can be prevented.

As the compound (III), the compounds described later in the examples and the following new compounds may be mentioned.

$CClF_2CClFO(CF_2)_4COF$

$CF_2ClCFCl(CF_2)_2O(CF_2)_2COF$

[The Method of Obtaining the Material Compound (I)]

The method of obtaining the compound (I) is not limited, and a known compound (I) may be used or may be produced from a known compound. As the compound (I), compounds having various structures corresponding to the objective compounds are readily available. They are also available by the following material production route-1. The compound (B) wherein $R^{H1}$— is $CX^1X^2=CX^3$— among the compound (I) will be also obtained by the material production route-2.

The material production route-1 is a method of producing the compound (I) by reacting the following compound (A1) with the following compound (A2). In the following formula, X is a halogen atom, and $R^{H1}, E^{H1} R^{H2}$ and $R^{H3}$ are the same as defined above.

$(R^{H1}—E^{H1}—)CR^{H2}R^{H3}CH_2—OH$ (A1)

$XCOR^{HB}$ (A2)

On the other hand, the material production route-2 is a method of producing the compound (IB) wherein $R^{H1}$— is $CX^1X^2ClCX^3Cl$—, by reacting the following compound (B1) with the following compound (B2) to form the following compound (B3), followed by reacting the following compound (B3) with a chlorinating agent. The symbols in the following formulae mean the same as defined above, and $X^{10}$ is a halogen atom, or a hydroxyl group.

$(CX^1X^2=CX^3—E^{H1}—)CR^{H2}R^{H3}CH_2—OH$ (B1)

$X^{10}COR^{HB}$ (B2)

$(CX^1X^2=CX^3—E^{H1}—)CR^{H2}R^{H3}CH_2—OCOR^{HB}$ (B3)

$(CX^1X^2ClCX^3Cl—E^{H1}—)CR^{H2}R^{H3}CH_2—OCOR^{HB}$ (IB)

In the above-mentioned material production route-1 and route-2, a reaction of the compound (A1) with the compound (A2) and a reaction of the compound (B1) with the compound (B2) can be carried out under an usual esterification reaction condition. While these reaction may be conducted in the presence of a solvent (hereinafter referred to as solvent 4), it is preferred to carried out in the absence of the solvent 4 from the view point of the volume efficiency. When solvent 4 is used, it is preferably a halogenated hydrocarbon solvent such as dichloromethane and chloroform. The amount of the solvent 4 is preferably from 0.5 to 5 times, relative to the total mass of the compound (A1) and the compound (A2) (or the compound (B1) and the compound (B2)).

Specific examples of the material production routes will be shown in the Examples described later. Among the compounds described in the Examples, the following compounds are new compounds.

$CHCl=CClO(CH_2)_5OH$ $CH_2=CH(CH_2)_2OCH_2CH_2CH_2OH$ $CH_2=CH(CH_2)_2OCOCF_2CFClCF_2Cl$ $CH_2=CH(CH_2)_2OCH(CH_3)CH_2OCOCF(CF_3)$ $OCF_2CF_2CF_3$

In the esterification reaction described above, HX is formed as a by-product. When the compound (A2) or the compound (B2) wherein X is a fluorine atom is used, HF will be formed. As a scavenger for such an HF, an alkali metal fluoride (such as sodium fluoride) or a base such as trialkylamine and pyridine may be present in the reaction system. The amount of the scavenger for HF is preferably from 1 to 10 mol times, relative the compound (A2) or the compound (B2). When a scavenger for HF is not used, it is preferred to remove HF from the reaction system by carrying with nitrogen gas.

In an usual case, the lower limit of the temperature of the esterification reaction is preferably −50° C. and the upper limit is preferably +100° C. or the boiling point of the solvent 4, whichever is lower. The reaction time is adjusted depending upon the feeding speed of the material and amount of the compound to be used in the reaction, and the reaction pressure is preferably from 0 to 2 MPa.

The compound (B3) formed by the reaction of the compound (B1) with the compound (B2) is reacted with a chlorinating agent to form the compound (IB). The reaction can be carried out under methods and conditions in a usual chlorination reaction. The chlorinating agent is preferably chlorine ($Cl_2$). When chlorine is used, the amount is preferably from 1 to 10 mol times, especially preferably from 1 to 5 mol times, relative the compound (B3). Although the reaction of the compound (B3) with a chlorinating agent may be conducted in the presence of a solvent (hereinafter referred to as solvent 5), it is preferred to conduct in the absence of the solvent 5 from the viewpoint of the volume efficiency. When solvent 5 is used, it is preferably a halogenated hydrocarbon solvent such as dichloromethane and chloroform. The amount of the solvent 5 is preferably from 0.5 to 5 times, relative to the mass of the compound (B3). The reaction temperature is preferably from −78° C. to +200° C.

The crude product containing the compound (I) produced by the method described above may be employed in the next reaction as a purified substance after the purification, or as it is. The method of purifying the crude product containing the compound (I) may be the one such as a method of distilling the crude product as it is, a method of separating the crude product phase after treated with a diluted aqueous alkali solution and a method of distilling the crude product after extracted by an appropriate organic solvent.

Further, the process of the present invention can be made to be the following efficient processes 1 to 3 by selecting the kinds of the groups in the compound (I)-(IV) in order to omit a separation step of the compound or modifying the process to a continuous process. In the following, the groups not defined there have the same meaning as described above.

[Process 1]

A process wherein groups are selected so that the compound (III) and the compound (IV) will be the same compound. By this process, the separation step of the product can be omitted. This process is partially in common with Process 3, and will be explained later in Process 3.

[Process 2]

A process wherein $R^{HB}$ is selected so that the compound (IV) will be of the same structure as the compound (A2) or the compound (B2). According to such a process, the resulting compound (IV) can be used again for the reaction with the compound (A1) or the compound (B1), whereby the process of the present invention can be made to be a continuous production process.

A specific example of the process may be the one wherein a perhalogeno group is used as $R^{HB}$ in the compound (A2) or the compound (B2). For example, when the compound (A2-1) is used as the compound (A), the process can be made to be the following production process.

For example, in the following production route using the compound (A1-1) and the compound (A2-1), the route is a continuous production process by using the resulting compound (A2-1) again in the reaction the with the compound (A1-1)

| | |
|---|---|
| $CH_3(CH_2ClCHCl(CH_2)_2O)CHCH_2OH$ | (A1-1) |
| $+FCOCF(CF_3)OCF_2CF_2CF_3$ | (A2-1) |
| $\rightarrow CH_3(CH_2ClCHCl(CH_2)_2O)CHCH_2\text{-}OCOCF(CF_3)OCF_2CF_2CF_3$ | (I-1) |
| $\rightarrow CF_3(CF_2ClCFClCF_2CF_2O)CFCF_2\text{-}OCOCF(CF_3)OCF_2CF_2CF_3$ | (II-1) |
| $\rightarrow CF_3(CF_2ClCFClCF_2CF_2O)CFCOF(III\text{-}1)+\text{compound}$ | (A2-1) |

$CF_3(CF_2ClCFClCF_2CF_2O)CFCOF$ can be led to be a material ($CF_2=CFCF_2CF_2OCF=CF_2$) for a fluorinated resin by a known method.

Similarly, in the following production route using the compound (A1-2) and the compound (A2-2), the route is a continuous production process by using the resulting compound (A2-2) again in the reaction with the compound (A1-2).

| | |
|---|---|
| $CH_2ClCHCl(CH_2)_2OH$ (A1-2)+$FCOCF_2CF_3$ | (A2-2) |
| $\rightarrow CH_2ClCHCl(CH_2)_2OCOCF_2CF_3$ | (I-2) |
| $\rightarrow CF_2ClCFClCF_2CF_2OCOCF_2CF_3$ | (II-2) |
| $\rightarrow CF_2ClCFClCF_2COF(III\text{-}2)+\text{Compound}$ | (A2-2) |

[Process 3]

A process wherein groups are selected so that the resulting compound (III) will be of the same structure as the compound (IV) and further, they will be of the same structure as the compound (A2) or the compound (B2). Such a process is particularly preferred since it is unnecessary to separate the product, and a part or whole of the formed product can be used again for the reaction with the compound (A2) or the compound (B2), whereby the process can be made to be a continuous process.

For example, a continuous production process for producing the compound (A2-3) by the following production route using the compound (A1-2) and the compound (A2-3) can be mentioned.

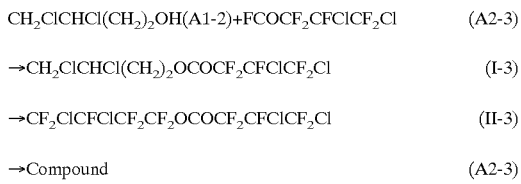

CH$_2$ClCHCl(CH$_2$)$_2$OH(A1-2)+FCOCF$_2$CFClCF$_2$Cl      (A2-3)

→CH$_2$ClCHCl(CH$_2$)$_2$OCOCF$_2$CFClCF$_2$Cl      (I-3)

→CF$_2$ClCFClCF$_2$CF$_2$OCOCF$_2$CFClCF$_2$Cl      (II-3)

→Compound      (A2-3)

EXAMPLES

In the following, the present invention will be described in detail with reference to examples, but the present invention is not limited thereto. Further, in the following, several terms are referred to as their respective abbreviations. gas chromatography: GC, gas chromatography mass analysis: GC-MS, tetramethylsilane: TMS, N,N-dimethylformamide: DMS, dichloropentafluoropropane: AK-225, 1,1,2-trichloro-1,2,2-trifluoroethane: R-113, liter:L. GC purity means the purity determined from the peak area ratio of GC.

Example 1
Productions of CF$_2$ClCFClCF$_2$CF$_2$OCF(CF$_3$)COF and FCOCF (CF$_3$)OCF$_2$CF$_2$CF$_3$

Example 1-1
Production of CH$_3$CH(O(CH$_2$)$_2$CH=CH$_2$)COO(CH$_2$)$_2$CH=CH$_2$ CH$_3$CHClCOOH (50 g)and CH$_2$=CH(CH$_2$)$_2$OH (75 ml) were put into a flask and stirred and 10 ml of concentrated sulfuric acid was added dropwise thereto over period of 10 minutes at room temperature. The resulting reaction solution was added to 250 ml of a saturated sodium carbonate aqueous solution. Water (150 ml) and tert-butyl methyl ether (150 ml) were added thereto, followed by liquid separation to obtain a tert-butyl methyl ether layer as an organic layer. Further, the organic layer was washed with 150 ml of water, dried over magnesium sulfate and then subjected to filtration to obtain a crude liquid. The crude liquid was concentrated to obtain CH$_3$CHClCOO(CH$_2$)$_2$CH=CH$_2$.

CH$_2$=CH(CH$_2$)$_2$OH (16.6 g) and DMF (120 ml) were put into another flask and cooled to maintain the internal temperature at from 8 to 9° C. A sodium hydrogen carbonate (10 g) was added thereto over a period of 30 minutes, and cooled again after stirred for 30 minutes at room temperature. Then, CH$_3$CHClCOO(CH$_2$)$_2$CH=CH$_2$ (50 g), which had been obtained earlier, dissolved in 30 ml of DMF was added dropwise thereto over 1.5 hours. After completion of the dropwise addition, heating was continued for 3 hours while maintaining the internal temperature at from 80 to 85° C. After cooled to the room temperature (25° C.), 200 ml of 2 mol/l hydrochloric acid was added thereto. An organic layer was obtained by extracting with 400 ml of the hexane/ethyl acetate=2/1 solution by 4 times. The organic layer was concentrated, washed twice by 500 ml of water, dried over magnesium sulfate, filtered and then concentrated again to obtain 86 g of CH$_3$CH(O(CH$_2$)$_2$CH=CH$_2$)COO(CH$_2$)$_2$CH=CH$_2$. Its GC purity was 83%. NMR spectrum was as follows.

$^1$H-NMR (399.8 MHz, solvent: CDCl$_3$, standard: TMS)δ (ppm): 1.39 (d, J=7.0 Hz, 3H), 2.33–2.45 (m, 4H), 3.41 (dt, J=7.0, 9.1 Hz, 1H), 3.63 (dt, J=7.0, 9.1 Hz, 1H), 3.96 (q, J=7.0 Hz, 1H), 4.15–4.27 (m, 2H), 5.02–5.14 (m, 4H), 5.73–5.88 (m, 2H).

Example 1-2
Production of CH$_3$CH(O(CH$_2$)$_2$CH=CH$_2$)CH$_2$OH

In an argon atmosphere, 6.9 g of lithium aluminum hydride and 240 ml of dehydrated diethyl ether were put into a flask and stirred in an ice bath. CH$_3$CH(O(CH$_2$)$_2$CH=CH$_2$)COO(CH$_2$)$_2$CH=CH$_2$(36 g) with GC purity of 83% obtained by EXAMPLE 1-1 was added dropwise thereto over a period of 45 minutes and stirred for 3.5 hours. Further, 100 ml of iced water was added thereto dropwise in a ice bath, and then 100 ml of water was added thereto and raised to room temperature (25° C.), followed by filtration. The resulting cake was washed with 450 ml of diethyl ether and the filtrate was separated. The water layer was extracted twice with 200 ml of diethyl ether to obtain a collected diethylether layer as an organic layer. The organic layer was dried over magnesium sulfate and subjected to filtration to obtain a crude liquid. The crude liquid was concentrated to 35 g and then was distilled under the reduced pressure to remove 6.6 g of the fraction with from 28 to 49° C./9.33 kPa, whereby 19.2 g of CH$_3$CH(O(CH$_2$)$_2$CH=CH$_2$)CH$_2$OH from the resulting fraction. Its GC purity was 98%. NMR spectrum was as follows.

$^1$H-NMR (399.8 MHz Solvent: CDCl$_3$, standard: TMS)δ (ppm): 1.12 (d, J=6.2 Hz, 3H), 2.35 (t q, J=1.3, 6.7 Hz, 2H), 3.42–3.48 (m, 2H), 3.51–3.59 (m, 2H), 3.64–3.69 (m, 1H), 5.04–5.15 (m, 2H), 5.79–5.89 (m, 1H).

Example 1-3
Production of CH$_3$CH(O(CH$_2$)$_2$CH=CH$_2$)CH$_2$OCOCF(CF$_3$)OCF$_2$CF$_2$CF$_3$ CH$_3$CH(O(CH$_2$)$_2$CH=CH$_2$)CH$_2$OH (19.2 g) having a GC purity of 98% obtained in EXAMPLE 1-2 was put into a flask and stirred while bubbling nitrogen gas. FCOCF(CF$_3$)OCF$_2$CF$_2$CF$_3$(50 g) was added dropwise thereto over 1 hour while maintaining the internal temperature at from 25 to 30° C. After completion of the dropwise addition, stirring was continued at room temperature for 3 hours and 80 ml of a saturated sodium hydrogen carbonate aqueous solution was added thereto at the internal temperature of not higher than 15° C.

Water (50 ml) and chloroform (100 ml) were added thereto, followed by liquid separation to obtain an organic layer. The organic layer was washed with 100 ml of water twice, dried over magnesium sulfate and subjected to filtration to obtain a crude liquid. The crude liquid was concentrated and purified by a silica gel column chromatography (eluent: hexane/ethyl acetate=4/1), followed by purification by a silica gel column chromatography (eluent: AK-225), to obtain 37 g of CH$_3$CH(O(CH$_2$)$_2$CH=CH$_2$)CH$_2$OCOCF(CF$_3$)OCF$_2$CF$_2$CF$_3$. Its GC purity was 99%. NMR spectra were as follows.

$^1$H-NMR (399.8 MHz, solvent: CDCl$_3$, standard: TMS)δ (ppm): 1.2 (d d, J=1.2, 6.4 Hz, 3H), 2.29 (q, J=6.7 Hz, 2H), 3.45–3.51 (m, 1H), 3.53–3.59 (m, 1H), 3.67–3.73 (m, 1H), 4.25–4.29 (m, 1H), 4.35–4.41 (m, 1H), 5.01–5.10 (m, 2H), 5.75–5.85 (m, 1H).

$^{19}$F-NMR (376.2 MHz, solvent CDCl$_3$, standard: CFCl$_3$)δ (ppm): −80.5 (1 F), −81.9 (3 F), −82.7 (3 F), −86.9 (1 F), −130.3 (2 F), −132.2 (1 F).

Example 1-4
Production of CH$_3$CH(O(CH$_2$)$_2$CHClCH$_2$Cl)CH$_2$OCOCF(CF$_3$)OCF$_2$CF$_2$CF$_3$ CH$_3$CH(O(CH$_2$)$_2$CH=CH$_2$)CH$_2$OCOCF(CF$_3$)OCF$_2$CF$_2$CF$_3$ (36 g) having a CC purity of 99% obtained in EXAMPLE 1-3 was put into a flask and stirred in an ice bath. Chlorine gas (9.5 g) was blown thereinto over 3 hours while maintaining the internal temperature at from 0 to 5° C.

Stirring was continued for 1 hour at room temperature while blowing nitrogen gas thereinto. The resulting reaction product was purified by a silica gel column chromatography (eluent: AK-225), to obtain 22 g of $CH_3CH(O(CH_2)_2CHClCH_2Cl)CH_2OCOCF(CF_3)OCF_2CF_2CF_3$. Its GC purity was 88%. NMR spectra were as follows.

$^1$H-NMR (399.8 MHz solvent: $CDCl_3$, standard: TMS)δ (ppm): 1.21 (dd, J=1.3, 6.3 Hz , 3H), 1.81–1.93 (m, 1H), 2.19–2.26 (m, 1H), 3.59–3.65 (m, 1H), 3.68–3.80 (m, 4H), 4.20–4.46 (m, 3H).

$^{19}$F-NMR (376.2 MHz, solvent $CDCl_3$, standard: $CFCl_3$)δ (ppm): −80.3 (1 F), −81.6 (3 F), −82.4 (3 F), −86.7 (1 F), −130.0 (2 F), −132.0 (1 F).

Example 1-5
Production of $CF_2ClCFClCF_2CF_2OCF(CF_3)CF_2OCOCF(CF_3)OCF_2CF_2CF_3$ Into a 500 ml autoclave made of nickel, R-113 (313 g) was added, stirred and maintained at 25° C. At the gas outlet of the autoclave, a condenser maintained at 20° C., a NaF packed layer and a condenser maintained at −10° C. were installed in series. Further, a liquid returning line was installed to return the condensed liquid from the condenser maintained at −10° C. to the autoclave. Nitrogen gas blown thereinto for 1.3 hours, and then 20% fluorine gas diluted with nitrogen gas was blown thereinto for about 1 hour at flow rate of 5.77 L/h. Then, while blowing the 20% fluorine gas at the same rate, a solution of $CH_3CH(O(CH_2)_2CHClCH_2Cl)CH_2OCOCF(CF_3)OCF_2CF_2CF_3$ (4.63 g) obtained in EXAMPLE 1-4 dissolved in R-113 (100 g) was injected over a period of 7.3 hours.

Then, while blowing the 20% fluorine gas diluted with nitrogen gas at the same rate, a R-113 solution having a benzene concentration of 0.01 g/ml was injected in an amount of 6 ml while raising the temperature from 25° C. to 40° C., whereupon the benzene injection inlet of the autoclave was closed and further an outlet valve was closed, followed by closing the fluorine gas inlet valve, when the internal pressure of the autoclave reached at 0.20 MPa. Stirring was continued for 1 hour. Then, while maintaining the internal pressure of the autoclave at atmospheric pressure and the internal temperature of the reactor at 40° C., 3 ml of the above-mentioned benzene solution was injected, the benzene injection inlet of the autoclave was closed, whereupon the benzene injection inlet of the autoclave was closed, and further an outlet valve was closed, followed by closing the fluorine gas inlet valve, when the internal pressure of the autoclave reached at 0.20 MPa. Stirring was continued for 1 hour.

Further, the same operation was repeated seven times. The total amount of benzene injected was 0.288 g, and the total amount of R-113 injected was 29 ml. Further, nitrogen gas was blown thereinto for 1.5 hours. The objective product was quantitatively analyzed by $^{19}$F-NMR, whereby the yield of the identified product was 63%.

$^{19}$F-NMR (376.0 MHz, solvent: $CDCl_3$, standard: $CFCl_3$)δ (ppm): −64.7 (2 F), −76.5~−80.0 (1 F), −80.0~−81.0 (4 F), −82.2 (3 F), −82.5 (3 F), −82.0~−82.9 (1 F), −86.4~−88.1 (3 F), −117.0~−119.7 (2 F), −130.4 (2 F), −131.9 (1 F), −132.3 (1 F), −145.9 (1 F).

Example 1-6
Production of $CF_2ClCFClCF_2CF_2OCF(CF_3)COF$ $CF_2ClCFClCF_2CF_2OCF(CF_3)CF_2OCOCF(CF_3)OCF_2CF_2CF_3$ (1.2 g) obtained in EXAMPLE 1-5 was charged into a flask together with NaF powder (0.01 g) and heated at 120° C. for 5 hours in an oil bath with vigorous stirring. At an upper portion of the flask, a reflux condenser adjusted at a temperature of 20° C. was installed. After cooling, the liquid sample (1.2 g) was recovered. By GC-MS, it was confirmed that the above-identified product was the main product. The NMR yield of the above-identified product was 72.3%.

Example 2
Production of $CClF_2CClFO(CF_2)_4COF$ and $FCOCF(CF_3)OCF_2CF_2CF_3$

Example 2-1
Production of $CHCl=CClO(CH_2)_5OH$

Into a 500 ml four necked flask, tetrahydrofuran (THF, 160 ml) and sodium hydride (60%, 24 g) were charged and stirred, and $HO(CH_2)_5OH$ (260 g) was added dropwise under cooing on an ice bath. After completion of dropwise adding, stirring was continued at room temperature for 1 hour. Then, $CHCl=CCl_2$ (66 g) was added dropwise thereto over 5 minutes. After completion of dropwise adding, stirring was continued at the bath temperature of 70° C. for 2.5 hours. After cooled to room temperature, water (400 ml) and methylene chloride (400 ml) were added thereto under cooling on an ice bath, followed by liquid separation to obtain a methylene chloride layer as an organic layer. Further, after the organic layer was washed with water (400 ml), and dried over MS4A, the crude product as it is was employed in the step of EXAMPLE 2-2.

$^1$H-NMR (300.4 MHz, solvent: $CDCl_3$, standard: TMS)δ (ppm): 1.37~1.79 (m, 6H), 3.64 (t, J=6.3 Hz, 2H), 4.00 (t, J=6.5 Hz, 2H), 5.47 (s, 1H).

Example 2-2
Production of $CHCl=CClO(CH_2)_5OCOCF(CF_3)OCF_2CF_2CF_3$ $CHCl=CCl(CH_2)_5OH$ (13 g) obtained in EXAMPLE 2-1 and triethylamine (25 g) were put into a flask and stirred in an ice bath. $FCOCF(CF_3)OCF_2CF_2CF_3$ (41 g) was added dropwise over 1 hour while maintaining the internal temperature not higher than 10° C. After completion of dropwise adding, stirring was continued at room temperature for 2 hours, and 30 ml of water was added thereto at the internal temperature not higher than 15° C.

The resulting crude liquid was subjected to liquid separation, and the lower layer obtained was washed twice with 50 ml of water, dried over magnesium sulfate, followed by filtration to obtain a crude liquid. By distilling under a reduced pressure, $CHCl=CClO(CH_2)_5OCOCF(CF_3)OCF_2CF_2CF_3$ (19 g) was obtained as a fraction of from 118 to 120° C./0.5 kPa. Its GC purity was 77%.

$^1$H-NMR (300.4 MHz, solvent: $CDCl_3$, standard: TMS)δ (ppm): 1.41~1.83 (m, 6H), 4.00 (t, J=6.0 Hz, 2H) 4.29~4.45 (m, 2 H), 5.48 (s, 1H).

$^{19}$F-NMR (282.7 MHz, solvent: $CDCl_3$, standard: $CFCl_3$)δ (ppm): −79.9 (1 F), −81.4 (3 F), −82.2 (3 F), −86.5 (1 F), −129.5 (2 F), −131.5 (1 F).

Example 2-3
Production of $CClF_2CClFO(CF_2)_5OCOCF(CF_3OCF_2CF_2CF_3$

Into a 500 ml autoclave made of nickel, R-113 (312 g) was added, stirred and maintained at 25° C. At the gas outlet of the autoclave, a condenser maintained at 20° C., a NaF packed layer and a condenser maintained at −10° C. were installed in series. Further, a liquid returning line was installed to return the condensed liquid from the condenser maintained at −10° C. to the autoclave. Nitrogen gas blown thereinto for 1.0 hours, and then 20% fluorine gas diluted with nitrogen gas was blown thereinto for about 1 hour at flow rate of 7.40 L/h. Then, while blowing the 20% fluorine gas at the same rate, a solution of CHCl=CClO(CH$_2$)$_5$ OCOCF(CF$_3$)OCF$_2$CF$_2$CF$_3$ (3.37 g) obtained in EXAMPLE 2-2 dissolved in R-113 (100 g) was injected over a period of 5.3 hours.

Then, while blowing the 20% fluorine gas diluted with nitrogen gas at the same rate, a R-113 solution having a benzene concentration of 0.01 g/ml was injected in an amount of 6 ml while raising the temperature from 25° C. to 40° C., whereupon the benzene injection inlet of the autoclave was closed and further an outlet valve was closed, followed by closing the fluorine gas inlet valve, when the internal pressure of the autoclave reached at 0.20 MPa. Stirring was continued for 0.9 hours. Then, while maintaining the internal pressure of the autoclave at atmospheric pressure and the internal temperature of the reactor at 40° C., 3 ml of the above-mentioned benzene solution was injected, the benzene injection inlet of the autoclave was closed, whereupon the benzene injection inlet of the autoclave was closed and further an outlet valve was closed, followed by closing the fluorine gas inlet valve, when the internal pressure of the autoclave reached at 0.20 MPa. Stirring was continued for 0.9 hours.

Further, the same operation was repeated one time. The total amount of benzene injected was 0.192 g, and the total amount of R-113 injected was 18 ml. Further, nitrogen gas was blown thereinto for 1.5 hours. The objective product was quantitatively analyzed by $^{19}$F-NMR, whereby the yield of the identified product was 73%.

$^{19}$F-NMR (376.0 MHz, solvent: CDCl$_3$, standard: CFCl$_3$)δ (ppm): −71.5 (2 F), −77.3 (1 F), −80.1 (1 F), −82.1 (3 F), −82.3 (3 F), −83.4 (1 F), −85.1 (1 F), −87.2 (2 F), −87.3 (1 F), −123.2 (2 F), −126.2 (2 F), −126.3 (2 F), −130.4 (2 F), −132.4 (1 F).

Example 2-4

Production of CClF$_2$CClFO(CF$_2$)$_4$COF

CClF$_2$CClFO(CF$_2$)$_5$OCOCF(CF$_3$)OCF$_2$CF$_2$CF$_3$ (0.8 g) obtained in EXAMPLE 2-3 was charged into a flask together with NaF powder (0.01 g) and heated at 120° C. for 4 hours and at 140° C. for 12.3 hours in an oil bath with vigorous stirring. At an upper portion of the flask, a reflux condenser adjusted at a temperature of 20° C. was installed. After cooling, the liquid sample (0.7 g) was recovered. By GC-MS, it was confirmed that CF$_3$CF(OCF$_2$CF$_2$CF$_3$)COF and the above-identified compound were the main products. The NMR yield of the above-identified product was 54.9%.

$^{19}$F-NMR (376.0 MHz, solvent: CDCl$_3$, standard: CFCl$_3$)δ (ppm): 24.9 (1 F), −71.3 (2 F), −77.1 (1 F), −83.1 (1 F), −84.9 (1 F), −118.8 (2 F), −123.1 (2 F), −125.6 (2 F).

Example 3

Production of CF$_2$ClCFCl(CF$_2$)$_2$O(CF$_2$)$_2$COF and FCOCF (CF$_3$)OCF$_2$CF$_2$CF$_3$ Example 3-1

Production of CH$_2$=CH(CH$_2$)$_2$OTs(Ts is p-toluene sulfonyl group.)

In a reactor 3-buten-1-ol (33.2 g) and pyridine (230 ml) were charged and p-toluene sulfonyl chloride (96.7 g) was added thereto over 3.5 hours, while maintaining the internal temperature not higher than 5° C. under cooling in an ice bath. After stirring for 30 minutes, the reaction mixture was added to water (250 ml). Dichloromethane (250 ml) was added thereto and subjected to liquid separation. A saturated aqueous sodium carbonate solution (250 ml) and water (200 ml) were added to wash the lower layer, followed by liquid separation and washing with water (200 ml) twice, and dried over magnesium sulfate. After filtration followed by distillation to remove the solvent, 98.1 g of CH$_2$=CH(CH$_2$)$_2$OTs was obtained.

$^1$H-NMR (300.4 MHz, solvent: CDCl$_3$, standard: TMS)δ (ppm): 2.36~2.43 (m, 2H), 2.43 (s, 3H), 4.06 (t, J=6.6 Hz, 2H), 5.04~5.11 (m, 2H), 5.60~5.66 (m, 1H), 7.34 (d, J=8.4 Hz, 2H), 7.77 (d, J=8.1 Hz, 2H).

Example 3-2

Production of CH$_2$=CH(CH$_2$)$_2$O(CH$_2$)$_3$OH

Into a reactor, 1,3-propanediol (46.7 g) and potassium hydroxide (34.5 g) were charged and stirred, and heated at the internal temperature of 75° C. for 30 minutes. At the internal temperature of 80° C., CH$_2$=CH(CH$_2$)$_2$OTs (69.5 g) obtained in EXAMPLE 3-1 was added thereto over 3 hours and standed as it is after stirring for 1 hour. The reaction mixture was poured into water (250 ml) and neutralized by adding hydrochloric acid. After filtration, the filtrate was extracted with t-butyl methyl ether (300 ml) four times. The organic layer put together was dried over magnesium sulfate and subjected to filtration, and the solvent was distilled off to obtain 5.5 g of CH$_2$=CH(CH$_2$)$_2$O(CH$_2$)$_3$OH.

$^1$H-NMR (300.4 MHz, solvent: CDCl$_3$, standard: TMS)δ (ppm): 1.83 (dt, J=5.4 Hz, 11 Hz, 2H), 2.34 (m, 2H), 2.6 (bs, 1H), 3.50 (t, J=6.6 Hz, 2H), 3.63 (t, J=6.0 Hz, 2H), 3.77 (t, J=5.4 Hz, 2H), 5.03~5.13 (m, 2H), 5.81 (ddt, J=6.6, 11, 17 Hz, 1H).

Example 3-3

Production of CH$_2$=CHCH$_2$CH$_2$OCH$_2$CH$_2$CH$_2$OCF(CF$_3$) OCF$_2$CF$_2$CF$_3$ CH$_2$=CH(CH$_2$)$_2$O(CH$_2$)$_3$OH (8.3 g) having a GC purity of 98% obtained in EXAMPLE 3-2 and triethylamine (13.6 g) were put into a flask and stirred in an ice bath. FCOCF (CF$_3$)OCF$_2$CF$_2$CF$_3$(30 g) was added dropwise thereto over 1 hour while maintaining the internal temperature not higher than 10° C. After completion of dropwise adding, stirring was continued at room temperature for 2 hours, and 50 ml of water was added thereto at the internal temperature not higher than 15° C.

The resulting crude liquid was subjected to liquid separation, and the lower layer obtained was washed twice with 50 ml of water, dried over magnesium sulfate, followed by filtration to obtain a crude liquid. The crude liquid was purified by a silica gel column chromatography (eluent: AK-225), to obtain CH$_2$=CHCH$_2$CH$_2$OCH$_2$CH$_2$CH$_2$OCF (CF$_3$)OCF$_2$CF$_2$CF$_3$ (18.5 g). Its GC purity was 97%.

$^1$H-NMR (300.4 MHz, solvent: CDCl$_3$, standard: TMS)δ (ppm): 1.93~2.01 (m, 2H), 2.26~2.34 (m, 2H), 3.42~3.49 (m, 4H), 4.41~4.54 (m, 2H), 5.02 (d, J=10.3 Hz, 1H), 5.07 (d, J=17 Hz, 1H), 5.72~5.85 (m, 1H).

$^{19}$F-NMR (282.7 MHz, solvent: CDCl$_3$, standard: CFCl$_3$)δ (ppm): −79.9 (1 F), −81.4 (3 F), −82.2 (3 F), −86.6 (1 F), −129.6 (2 F), −131.5 (1 F).

Example 3-4

Production of CH$_2$ClCHClCH$_2$CH$_2$OCH$_2$CH$_2$CH$_2$OCF (CF$_3$)OCF$_2$CF$_2$CF$_3$ CH$_2$=CHCH$_2$CH$_2$OCH$_2$CH$_2$CH$_2$OCF(CF$_3$) OCF$_2$CF$_2$CF$_3$ (18.4 g) having a GC purity of 97% obtained in EXAMPLE 3-3 was put into a flask and stirred at −10° C. in an ice bath. Chlorine gas (4.4 g) of was blown thereinto over 1 hour while maintaining the internal temperature not higher than 0° C. Stirring was continued for 1 hour at room temperature while bubbling nitrogen gas thereinto to obtain CH$_2$ClCHClCH$_2$CH$_2$OCH$_2$CH$_2$CH$_2$OCF(CF$_3$) OCF$_2$CF$_2$CF$_3$ (19.8 g). The crude product obtained as it is was used in a step of EXAMPLE 3-5.

$^1$H-NMR (300.4 MHz, solvent: CDCl$_3$, standard: TMS)δ (ppm): 1.93~2.01 (m, 2H), 2.26~2.34 (m, 2H), 3.44 (t, J=6.6 Hz, 2H), 3.47 (t, J=6.0 Hz, 2H), 4.41~4.54 (m, 2H), 4.99~5.10 (m, 2H), 5.71~5.85 (m, 1H).

$^{19}$F-NMR (282.7 MHz, solvent: CDCl$_3$, standard: CFCl$_3$)δ (ppm): −79.9 (1 F), −81.3 (3 F), −82.2 (3 F), −86.6 (1 F), −129.5 (2 F), −131.5 (1 F).

Example 3-5
Production of CF$_2$ClCFCl(CF$_2$)$_2$O(CF$_2$)$_3$OCOCF(CF$_3$)OCF$_2$CF$_2$CF$_3$ Into a 500 ml autoclave made of nickel, R-113 (312 g) was added, stirred and maintained at 25° C. At the gas outlet of the autoclave, a condenser maintained at 20° C., a NaF packed layer and a condenser maintained at −10° C. were installed in series. Further, a liquid returning line was installed to return the condensed liquid from the condenser maintained at −10° C. to the autoclave. Nitrogen gas blown thereinto for 1.0 hour, and then 20% fluorine gas diluted with nitrogen gas was blown thereinto for about 1.5 hours at flow rate of 8.04 L/h. Then, while blowing the 20% fluorine gas at the same rate, a solution of CH$_2$ClCHClCH$_2$CH$_2$OCH$_2$CH$_2$CH$_2$OCF(CF$_3$)OCF$_2$CF$_2$CF$_3$ (4.44 g) obtained in EXAMPLE 3-4 dissolved in R-113 (100 g) was injected over a period of 5.3 hours.

Then, while blowing the 20% fluorine gas diluted with nitrogen gas at the same rate, a R-113 solution having a benzene concentration of 0.01 g/ml was injected in an amount of 6 ml while raising the temperature from 25° C. to 40° C., whereupon the benzene injection inlet of the autoclave was closed and further a outlet valve was closed, followed by closing the fluorine gas inlet valve, when the internal pressure of the autoclave reached at 0.20 MPa. Stirring was continued for 0.4 hours. Then, while maintaining the internal pressure of the autoclave at atmospheric pressure and the internal temperature of the reactor at 40° C., 3 ml of the above-mentioned benzene solution was injected, the benzene injection inlet of the autoclave was closed, whereupon the benzene injection inlet of the autoclave was closed and further a outlet valve was closed, followed by closing the fluorine gas inlet valve, when the internal pressure of the autoclave reached at 0.20 MPa. Stirring was continued for 0.4 hours.

Further, the same operation was repeated seven times. The total amount of benzene injected was 0.303 g, and the total amount of R-113 injected was 30 ml. Further, nitrogen gas was blown thereinto for 1.5 hours. The objective product was quantitatively analyzed by $^{19}$F-NMR, whereby the yield of the identified product was 45%.

$^{19}$F-NMR (376.0 MHz, solvent: CDCl$_3$, standard: CFCl$_3$)δ (ppm): −64.4 (2 F), −80.0 (1 F), −81.3 (2 F), −81.9 (3 F), −82.1 (3 F), −84.0 (2 F), −87.1 (1 F), −87.3 (2 F), −117.2~−119.4 (2 F), −129.4 (2 F), −130.3 (2 F), −131.8 (1 F), −132.3 (1 F).

Example 3-6
Production of CF$_2$ClCFCl(CF$_2$)$_2$O(CF$_2$)$_2$COF

CF$_2$ClCFCl(CF$_2$)$_2$O(CF$_2$)$_3$OCOCF(CF$_3$)OCF$_2$CF$_2$CF$_3$ (3.0 g) obtained in EXAMPLE 3-5 was charged into a flask together with NaF powder (0.06 g) and heated at 120° C. for 3.7 hours and at 140° C. for 12 hours in an oil bath with vigorous stirring. At an upper portion of the flask, a reflux condenser adjusted to 20° C. was installed. After cooling, the liquid sample (2.9 g) was recovered. By GC-MS, it was confirmed that FCOCF(CF$_3$)CF$_2$CF$_2$CF$_3$ and the above-identified product were the main products. The NMR yield of the above-identified product was 73.0%.

$^{19}$F-NMR (376.0 MHz, solvent: CDCl$_3$, standard: CFCl$_3$)δ (ppm): 24.3 (1 F), −64.8 (2 F), −81.7 (2 F), −86.4 (2 F), −118.8~−120.0 (2 F), −122.1 (2 F), −131.9 (1 F).

Example 4
Production of FCOCF$_2$CFClCF$_2$Cl and CF$_3$CF$_2$COF

Example 4-1
Production of CF$_3$CF$_2$COO(CH$_2$)$_2$CHClCH$_2$Cl

CH$_2$ClCHCl(CH$_2$)$_2$OH (30 g) was put into a flask and stirred while bubbling nitrogen gas. CF$_2$CF$_2$COF(310 g) was fed thereto over 3 hours while maintaining the internal temperature at from 25 to 30° C. After completion of the feeding, 50 ml of a saturated aqueous sodium hydrogen carbonate solution was added thereto at the internal temperature of not higher than 15° C. Chloroform (50 ml) were added thereto, followed by liquid separation to obtain the chloroform layer as an organic layer. Further, the organic layer was washed with 200 ml of water twice, dried over magnesium sulfate and subjected to filtration to obtain a crude liquid. The crude liquid was concentrated by an evaporator, followed by a distillation under reduced pressure to obtain a fraction (24 g) of from 73 to 75° C./0.9 kPa. The fraction was purified by a silica gel column chromatography (eluent: hexane/ethyl acetate=20/1) to obtain a purified product (18.8 g). Its GC purity was 98%. It was confirmed by NMR spectra that above-identified compound was a main product.

$^1$H-NMR (399.8 MHz, solvent: CDCl$_3$, standard: TMS)δ (ppm): 2.11 (m, 1H), 2.52 (m, 1H), 3.69 (dd, J=7.9, 11.4 Hz, 1H), 3.84 (dd, J=4.7, 11.4 Hz, 1H), 4.15 (m, 1H), 4.60 (m, 2H).

$^{19}$F-NMR (376.2 MHz, solvent: CDCl$_3$, standard: CFCl$_3$)δ (ppm): −83.8 (3 F), −122.5 (2 F).

Example 4-2
Production of CF$_3$CF$_2$COOCF$_2$CF$_2$CFClCF$_2$Cl

Into a 500 ml autoclave made of nickel, R-113 (201 g) was added, stirred and cooled at −10° C. Nitrogen gas blown thereinto for 1 hour, and then 20% fluorine gas diluted with nitrogen gas was blown thereinto for about 1 hour at flow rate of 5.66 L/h. Then, while blowing the 20% fluorine gas at the same rate, a solution of CF$_3$CF$_2$COO(CH$_2$)$_2$CHClCH$_2$Cl (6.58 g) obtained in EXAMPLE 4-1 dissolved in R-113 (134 g) was injected over a period of 6.9 hours.

Then, while blowing the 20% fluorine gas diluted with nitrogen gas at the same rate, a R-113 solution of benzene (0.01 g/ml) was injected thereto, whereupon an outlet valve was closed, when the internal pressure of the autoclave became 0.12 MPa, the inlet valve of the autoclave was closed, and stirring was continued for 1 hour. Similar operation of injecting benzene was repeated once while raising temperature from −10° C. to 40° C. and then eight times at 40° C. The total amount of benzene injected was 0.330 g, and the total amount of R-113 injected was 33 ml. Further, nitrogen gas was blown thereinto for 2 hours. The objective product was quantitatively analyzed by $^{19}$F-NMR, whereby the yield of the identified product was 51%.

$^{19}$F-NMR (376.2 MHz, solvent: CDCl$_3$, standard: CFCl$_3$)δ (ppm): −65.4 (2 F), −84.2 (3 F), −85.4 (2 F), −119.1 (2 F), −123.1 (2 F), −132.5 (1 F).

Example 4-3
Production of FCOCF$_2$CFClCF$_2$Cl

CF$_3$CF$_2$COOCF$_2$CF$_2$CFClCF$_2$Cl (1.5 g) obtained in EXAMPLE 4-2 was charged into a flask together with NaF powder (0.03 g) and heated at 120° C. for 5 hours in an oil bath with vigorous stirring. At an upper portion of the flask, a reflux condenser adjusted to a temperature of 20° C. was installed. After cooling, the liquid sample (0.8 g) and gas sample(0.6 g)was recovered. By GC-MS, it was confirmed that CF$_3$CF$_2$COF and the above-identified product were the main products. The NMR yield of the above-identified product was 75.1%.

Example 5
Production of a mixture of $CF_2ClCFClCF_2COF$ and $CF_2ClCF_2CFClCOF$

Example 5-1
Production of $CF_2ClCFClCF_2COO(CH_2)_2CHClCH_2Cl$ and $CF_2ClCF_2CFClCOO(CH_2)_2CHClCH_2Cl$ $CH_2ClCHCl(CH_2)_2OH$ (49.5 g) was put into a flask and stirred while bubbling nitrogen gas. A mixture (86.1 g) of $CF_2ClCClF_2COF$ and $CF_2ClCF_2CFClCOF$ in 89:11 (molar ratio) was added dropwise thereto over 1 hour and 40 minutes while maintaining the internal temperature at from 25 to 30° C. After completion of the adding, a saturated aqueous sodium hydrogen carbonate solution (100 ml) was added thereto at the internal temperature of not higher than 15° C. Chloroform (150 ml) was added thereto, followed by liquid separation to obtain the chloroform layer. Further, the chloroform layer was washed with 200 ml of water twice, dried over magnesium sulfate and subjected to filtration to obtain a crude liquid. The crude liquid was concentrated by an evaporator, followed by a distillation under reduced pressure to obtain a fraction (1) (55.4 g) of from 99 to 106° C./0.48 kPa and a fraction (2) (7.9 g) of from 100 to 109° C./0.47 kPa. Regarding the GC purity as a mixture, the fraction (1) was 85% and the fraction (2) was 84%.

The fraction (1) (9.4 g) was purified by a silica gel column chromatography (eluent: hexane/ethyl acetate=20/1) to obtain a purified product (7.5 g). Its GC purity was 98%. It was confirmed by NMR spectrum that a mixture of $CF_2ClCFClCF_2COO(CH_2)_2CHClCH_2Cl$ and $CF_2ClCF_2CFClCOO(CH_2)_2CHClCH_2Cl$ was a main product and their ratio was 87:13 (molar ratio).

$CF_2ClCFClCF_2COO(CH_2)_2CHClCH_2Cl$:

$^1$H-NMR (399.8 MHz, solvent: $CDCl_3$, standard: TMS)δ (ppm): 2.09 (m, 1H), 2.52 (m, 1H), 3.69 (d d, J=7.6, 11.4 Hz, 1H), 3.84 (dd, J=4.7, 11.4 Hz, 1H), 4.17 (m, 1H), 4.58 (m, 2 H).

$^{19}$F-NMR (376.2 MHz, solvent: $CDCl_3$, standard: $CFCl_3$)δ (ppm): −63.6 (1 F), −64.8 (1 F), −110.9 (1 F), −114.0 (1 F), −131 (1 F).

$CF_2ClCF_2CFClCOO(CH_2)_2CHClCH_2Cl$:

$^1$H-NMR (399.8 MHz, solvent: $CDCl_3$, standard: TMS)δ (ppm): 2.09 (m, 1H), 2.52 (m, 1H), 3.69 (dd, J=7.6, 11.4 Hz, 1H), 3.84 (dd, J=4.7, 11.4 Hz, 1H), 4.17 (m, 1H), 4.58 (m, 2 H).

$^{19}$F-NMR (376.2 MHz, solvent: $CDCl_3$, standard: $CFCl_3$)δ (ppm): −66.9 (1 F), −67.0 (1 F), −113.4 (1 F), −117.6 (1 F), −129.0 (1 F).

Example 5-2
Production of a mixture of $CF_2ClCFClCF_2COOCF_2CF_2CFClCF_2Cl$ and $CF_2ClCF_2CFClCOOCF_2CF_2CFClCF_2Cl$ Into a 500 ml autoclave made of nickel, R-113 (200 g) was added and stirred, and nitrogen gas was blown thereinto for 1 hour, and then 20% fluorine gas diluted with nitrogen gas was blown thereinto at room temperature for about 1 hour at flow rate of 5.66 L/h.

Then, while blowing the 20% fluorine gas at the same rate, a solution of a mixture of $CF_2ClCFClCF_2COO(CH_2)_2CHClCH_2Cl$ and $CF_2ClCF_2CFClCOO(CH_2)_2CHClCH_2Cl$ in 87:13 (molar ratio)obtained in EXAMPLE 5-1 dissolved in R-113 (243 g) was injected over a period of 11.5 hours.

Then, while blowing the 20% fluorine gas diluted with nitrogen gas at the same rate, a R-113 solution of benzene (0.01 g/ml) was injected thereto, whereupon a outlet valve was closed, when the internal pressure of the autoclave became 0.12 MPa, the inlet valve of the autoclave was closed, and stirring was continued for 1 hour. Further, similar operation of injecting benzene was repeated once while raising temperature from room temperature to 40° C. and then eight times at 40° C. The total amount of benzene injected was 0.342 g, and the total amount of R-113 injected was 33 ml. Further, nitrogen gas was blown thereinto for 2 hours. By analysis of the product with $^{19}$F-NMR, the yield of the identified product was 80%.

$CF_2ClCFClCF_2COOCF_2CF_2CFClCF_2Cl$:

$^{19}$F-NMR (564.6 MHz, solvent: $CDCl_3$, standard $CFCl_3$)δ (ppm): −64.4~−65.9 (2 F), −65.4 (2 F), −85.5~−86.3 (2 F), −111.1~−115.1 (2 F), −118.7~−120.1 (2 F), −132.0 (1 F), −132.5 (1 F).

$^{13}$C-NMR (150.8 MHz, solvent: $CDCl_3$, standard: $CDCl_3$)δ (ppm): 104.4, 104.5, 109.4, 110.8, 116.6, 124.3, 124.6, 152.0.

$CF_2ClCF_2CFClCOOCF_2CF_2CFClCF_2Cl$:

$^{19}$F-NMR (564.6 MHz, solvent: $CDCl_3$, standard: $CFCl_3$)δ (ppm): −64.4~−66.0 (2 F), −68.0 (2 F), −85.5~−86.3 (2 F), −113.7~−115.3 (2 F), −118.7~−120.1 (2 F), −130.0 (1 F), −132.5 (1 F).

$^{13}$C-NMR (150.8 MHz, solvent: $CDCl_3$, standard: $CDCl_3$)δ (ppm): 99.0, 104.4, 110.2, 110.8, 116.6, 122.8, 124.6, 153.2.

Example 5-3
Production of a mixture of $CF_2ClCFClCF_2COF$ and $CF_2ClCF_2CFClCOF$ A mixture (5.6 g) of $CF_2ClCFClCF_2COOCF_2CF_2CFClCF_2Cl$ and $CF_2ClCF_2CFClCOOCF_2CF_2CFClCF_2Cl$ obtained in EXAMPLE 5-2 was charged into a flask together with NaF powder (0.12 g) and heated at 140° C. for 5 hours in an oil bath with vigorous stirring. At an upper portion of the flask, a reflux condenser adjusted to a temperature of 20° C. was installed. After cooling, 5.2 g of the liquid sample was recovered. By GC-MS, it was confirmed that the above-identified product was the main product. The NMR yield of the above-identified product was 83.4%.

Example 6
Production of $CF_2ClCFClCF_2COF$

Example 6-1
Production of $CH_2=CHCH_2CH_2OCOCF_2CFClCF_2Cl$ $CH_2=CHCH_2CH_2OH$ (70.8 g) was put into a flask and stirred while bubbling nitrogen gas. A mixture (264.5 g) of $CF_2ClCFClCF_2COF$ and $CF_2ClCF_2CFClCOF$ in 89:11 (molar ratio) was added dropwise thereto over 1 hours while maintaining the internal temperature at from 25 to 30° C. After completion of the addition, stirring was continued for 4 hours at room temperature, and then, 500 ml of a saturated aqueous sodium hydrogen carbonate solution was added thereto at the internal temperature of not higher than 15° C. The resulting crude liquid was subjected to liquid separation to a fluorocarbon layer. Further, the fluorocarbon layer was washed with 200 ml of water twice, dried over magnesium sulfate and subjected to filtration to obtain a crude liquid. By a distillation under reduced pressure, 81.2 g of a fraction of from 69 to 72° C./1.0 kPa. The GC purity was 96%. NMR spectra were as follows.

$^1$H-NMR (300.4 MHz, solvent: $CDCl_3$, standard: TMS)δ ppm): 2.46~2.50 (m, 2H), 4.41 (t, J=6.6 Hz, 1H), 5.11~5.21 (m, 2H), 5.70~5.84 (m, 1H).

$^{19}$F-NMR (282.7 MHz, solvent: CDCl$_3$, standard: CFCl$_3$)δ (ppm): −62.9 (1 F), −64.1 (1 F), −110.1 (1 F), −113.1 (1 F), −130.4 (1 F).

Example 6-2

Production of CH$_2$ClCHClCH$_2$CH$_2$OCOCF$_2$CFClCF$_2$Cl

CH$_2$=CHCH$_2$CH$_2$OCOCF$_2$CFClCF$_2$Cl (80.0 g) having a GC purity of 96% obtained in EXAMPLE 6-1 was put into a flask and stirred in a bath of temperature of −10° C. Chlorine gas (24.5 g) was blown thereinto over 1.5 hours while maintaining the internal temperature not higher than 0° C. Stirring was continued for 1 hour at room temperature while bubbling nitrogen gas thereinto to obtain a crude liquid. The crude liquid was purified by a silica gel column chromatography (eluent: AK-225) to obtain CH$_2$ClCHClCH$_2$CH$_2$OCOCF$_2$CFClCF$_2$Cl (93.0 g) having a GC purity of 85%.

Example 6-3

Production of CF$_2$ClCFClCF$_2$CF$_2$OCOCF$_2$CFClCF$_2$Cl

Using CH$_2$ClCHClCH$_2$CH$_2$OCOCF$_2$CFClCF$_2$Cl (93.0 g) having a purity of 85% obtained in EXAMPLE 6-2 instead of 12.0 g of the mixture in EXAMPLE 5-2, and the other material in 7.7 times, the reaction was carried out in the same manner as in EXAMPLE 5-2 to obtain the identified compound with a yield of 80%.

Example 6-4

Production of CF$_2$ClCFClCF$_2$COF

Using CF$_2$ClCFClCF$_2$CF$_2$OCOCF$_2$CFClCF$_2$Cl (43.4 g) obtained in EXAMPLE 6-3 instead of 5.6 g of the mixture in EXAMPLE 5-3, and the other material in 7.7 times, the reaction was carried out in the same manner as in EXAMPLE 5-3 to obtain the identified compound with a yield of 84%.

Example 6-5

Continuous production of CF$_2$ClCFClCF$_2$COF

Using CF$_2$ClCFClCF$_2$COF obtained in EXAMPLE 6-4 instead of the mixture in EXAMPLE 6-1, the reaction was carried out in the same manner as in from EXAMPLE 6-1 to EXAMPLE 6-4 in this order to obtain CF$_2$ClCFClCF$_2$COF Example 7

Example 7-1

Continuous production of CH$_3$CH (O(CH$_2$)$_2$CH=CH$_2$)CH$_2$OH

By NMR spectrum, it was confirmed that the fraction of from 28 to 49° C./9.33 kPa obtained in EXAMPLE 1-2 was CH$_2$=CH(CH$_2$)$_2$OH. Using the above-mentioned fraction (75 ml), the reaction was carried out in the same manner as in from EXAMPLE 1-1 to EXAMPLE 1-4 to obtain CH$_3$CH (O(CH$_2$)$_2$CH=CH$_2$)CH$_2$OH.

Example 7-2

Continuous production of CF$_2$ClCFClCF$_2$CF$_2$O(CF$_2$)$_2$COF

The reaction product in EXAMPLE 3-6 was purified by a distillation at atmospheric pressure, and a fraction of 55° C. was obtained to be FCOCF(CF$_3$)OCF$_2$CF$_2$CF$_3$ (0.8 g). The fraction having high boiling points was preserved. Using the obtained FCOCF(CF$_3$)OCF$_2$CF$_2$CF$_3$, the reaction was carried out in the same manner as in from EXAMPLE 3-3 to EXAMPLE 3-6, followed by purification with an atmospheric distillation to obtain FCOCF(CF$_3$)OCF$_2$CF$_2$CF$_3$(0.7 g) as the fraction of 55° C. The residual high boiling point fraction was mixed with the preserved above-mentioned fraction having high boiling points, and then was purified by a distillation under atmospheric pressure to obtain CF$_2$ClCFClCF$_2$CF$_2$O(CF$_2$)$_2$COF (2.0 g) as a fraction of from 138 to 139° C.

Industrial Applicability

According to the present invention, it is possible to produce a vic-dichloro acid fluoride compound in a short process and in good yield from the compound (I) which is inexpensive and readily available. Particularly, according to the present invention, it is possible to produce a low molecular weight vic-dichloro acid fluoride compound and a complex structural vic-dichloro acid fluoride compound which used to be difficult to produce by a conventional process.

Further, the production process of the present invention is extensively applicable process which is not limited to the compounds described above as specific examples, but can be applied to various compounds, whereby a vic-dichloro acid fluoride compound having a faverite structure can be readily produced. Further, by selecting a structure of the substituent group, the production process of the present invention can be a continuous process.

Further, the compound (III) which can be produced by the process of the present invention has a moiety of CF$_2$ClCFCl- at the terminal. The moiety can be led to a polymerizable carbon-carbon double bond by a known method. For example, a vic-dichloro acid fluoride compound (CF$_2$ClCFClCF$_2$COF), which can be obtained by the process of the present invention, can be led to a perfluoro(3-butenyl vinyl ether) which is a monomer of a fluorinated resin. Perfluoro(3-butenyl vinyl ether) can be polymerized to produce a useful fluorinated resin which is excellency in heat resistance and chemical resistance and transparent.

Moreover, among the compound (III) and/or the compound (IV) obtained by the process of the present invention, the compound having a essential partial structure of [C$^1$F—C$^2$—COF] at the terminal of the molecule can be converted to [C$^1$=C$^2$] of the terminal by a known method (Methods of Organic Chemistry, 4, Vol. 10b, part 1, p 703, etc). This compound is also valuable material for a fluorinated resin. Namely, the compound (III) and/or the compound (IV) produced by the process of the present invention are useful compounds as precursors for fluorinated resins. Further, new compound provided by the present invention is useful compound as an intermediate compound for a precursor.

The entire disclosures of Japanese Patent Application No. 11-246154 filed on Aug. 31, 1999 and Japanese Patent Application No. 2000-211722 filed on Jul. 12, 2000 including specifications, claims and summaries are incorporated herein by reference in their entireties.

What is claimed is:

1. A process for producing a vic-dichloro acid fluoride compound comprising:

fluorinating compound (I) in a liquid phase to form compound (II), and dissociating an ester bond of the compound (II) to form compound (III), or compound (III) and compound (IV);

wherein compounds (I), (II), (III) and (IV) have the following formulas:

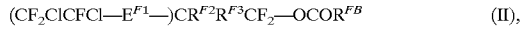

wherein,

R$^{H1}$ is CX$^1$X$^2$ClCX$^3$Cl— or CClX$^4$=CCl—, wherein each of X$^1$–X$^4$ is independently a hydrogen atom or a fluorine atom, R$^{H2}$ and RH$^{H3}$ are each, independently, a hydrogen atom, a fluorine atom, a monovalent saturated hydrocarbon group, a halogeno monovalent saturated hydrocarbon group, a hetero atom-containing monovalent saturated hydrocarbon group or a halogeno (hetero atom-containing monovalent saturated hydrocarbon) group, E$^{H1}$ is a bivalent connecting group or a single bond, E$^{F1}$ is a group corresponding to E$^{H1}$, and when E$^{H1}$ is a single bond, E$^{F1}$ is a single bond, and when E$^{H1}$ is a bivalent connecting group having one or more hydrogen atoms, E$^{F1}$ is a group corresponding to E$^{H1}$ wherein at least one hydrogen atom is fluorinated, and when E$^{H1}$ is a bivalent connecting group having no hydrogen atom, E$^{F1}$ is the same group as E$^{H1}$, R$^{HB}$— is a monovalent saturated hydrocarbon group, a halogeno monovalent saturated hydrocarbon group, a hetero atom-containing monovalent saturated hydrocarbon group or a halogeno(hetero atom-containing monovalent saturated hydrocarbon) group, R$^{F2}$, R$^{F3}$, and R$^{FB}$ are as follows:

R$^{F2}$ is a fluorinated R$^{H2}$ group,

R$^{F3}$ is a fluorinated R$^{H3}$ group,

R$^{FB}$ is a fluorinated R$^{HB}$ group, provided that, when one or more hydrogen atom(s) are present in R$^{H2}$, R$^{H3}$ or R$^{HB}$, then R$^{F2}$, R$^{F3}$ or R$^{FB}$ is a group corresponding to R$^{H2}$, R$^{H3}$ and R$^{HB}$, respectively, wherein at least one hydrogen is fluorinated, and when no hydrogen atom is present in R$^{H2}$, R$^{H3}$ or R$^{HB}$, then R$^{F2}$, R$^{F3}$ or R$^{FB}$ is a group corresponding to R$^{H2}$, R$^{H3}$ or R$^{HB}$ respectively, wherein the decomposition of the ester bond of compound (II) is conducted in the absence of solvent.

2. The process according to claim 1, wherein a molecular weight of the compound (I) ranges from 300 to 1000 and the fluorine content ranges from 30 to 86 mass %.

3. The process of claim 1, wherein the fluorination reaction is carried out by feeding an excess equivalent amount of fluorine relative to hydrogen atoms in compound (I) into the liquid phase to form compound (II) from the compound (I) in a liquid phase.

4. The process of claim 1, wherein a C—H bond-containing compound is present in a liquid phase in the reaction system of fluorination, or the fluorination reaction is carried out under ultra violet radiation.

5. The process of claim 1, wherein compound (I) is produced by reacting compound (A1) with compound (A2), provided that X is a halogen atom, and R$^{H1}$, E$^{H1}$, R$^{H2}$ and R$^{H3}$ have the same meaning as in claim 1, wherein (A1) and (A2) have the following formulas:

(R$^{H1}$—E$^{H1}$—)CR$^{H2}$R$^{H3}$CH$_2$—OH (A1),

XCOR$^{HB}$ (A2).

6. The process of claim 1, wherein compound (IB), which is compound (I) wherein R$^{H1}$ is CX$^1$X$^2$ClCX$^3$Cl —, is produced by:

reacting compound (B1) with compound (B2) to form the compound (B3), and then reacting the compound (B3) with a chlorinating agent, wherein X$^1$, X$^2$, X$^3$, E$^{H1}$, R$^{H2}$, R$^{H3}$ and R$^{H8}$ have the same meanings as in claim 1, and wherein (B1), (B2), (B3) and (IB) have the following formulas:

(CX$^1$X$^2$=CX$^3$—E$^{H1}$—)CR$^{H2}$R$^{H3}$ CH$_2$—OH (B1),

X$^{10}$COR$^{HB}$ (B2), wherein X$^{10}$ is a halogen atom or a hydroxyl group, (CX$^1$X$^2$=CX$^3$—E$^{H1}$—)CR$^{H2}$R$^{H3}$CH$_2$—OCOR$^{HB}$ (B3), (CX$^1$X$^2$ClCX$^3$Cl—E$^{H1}$—)CR$^{H2}$R$^{H3}$CH$_2$—OCOR$^{HB}$ (IB).

7. The process of claim 6, wherein the chlorinating agent is chlorine.

8. The process of claim 6, wherein compound (IV) and compound (B2) are the same compound.

9. The process of claim 5, wherein compound (IV) and compound (B2) are the same compound and a part or whole of the resulting compound (IV) is used again for the reaction with compound (A1) or compound (BI).

10. The process of claim 1, wherein compound (III) and compound (IV) are the same compound.

11. A compound represented by any one of the following formulae:

CHCl=CClO(CH$_2$)$_5$H,

CH$_2$=CH(CH$_2$)$_2$OCH$_2$CH$_2$CH$_2$OH,

CH$_2$=CH(CH$_2$)$_2$OCOCF$_2$CFClCF$_2$Cl,

CH$_2$=CH(CH$_2$)$_2$OCH(CH$_3$)CH$_2$OCOCF(CF$_3$)OCF$_2$CF$_2$CF$_3$,

CClH=CClO(CH$_2$)$_5$OCOCF(CF$_3$)OCF$_2$CF$_2$CF$_3$,

CClF$_2$CClFO(CF$_2$)$_5$OCOCF(CF$_3$)OCF$_2$CF$_2$CF$_3$,

CH$_2$=CH(CH$_2$)$_2$O(CH$_2$)$_3$OCOCF(CF$_3$)OCF$_2$CF$_2$CF$_3$,

CH$_2$ClCHCl(CH$_2$)$_2$O(CH$_2$)$_3$OCOCF(CF$_3$)OCF$_2$CF$_2$CF$_3$,

CF$_2$ClCFCl(CF$_2$)$_2$O(CF$_2$)$_3$OCOCF(CF$_3$)OCF$_2$CF$_2$CF$_3$, or

CF$_2$ClCFCl(CF$_2$)$_2$O(CF$_2$)$_2$COF.

12. The method of claim 1, wherein R$^{H1}$ is CX$^1$X$^2$ClCX$^3$Cl—.

13. The method of claim 1, wherein R$^{H1}$ is CClX$^4$=CCl—.

14. The method of claim 1, wherein E$^{H1}$ is a bivalent connecting group.

15. The method of claim 1, wherein E$^{H1}$ is a single bond.

16. The method of claim 1, wherein R$^{H2}$ and R$^{H3}$ are halogeno groups containing one or more halogen atoms other than fluorine.

17. The method of claim 1, wherein R$^{H2}$ and R$^{H3}$ are each, independently, a hydrogen atom, a fluorine atom, a monovalent saturated hydrocarbon group, or a hetero atom-containing monovalent saturated hydrocarbon group.

18. The method of claim 1, wherein R$^{H2}$ is a monovalent saturated hydrocarbon group, a halogeno monovalent saturated hydrocarbon group, a hetero atom-containing monovalent saturated hydrocarbon group or a halogeno (hetero atom-containing monovalent saturated hydrocarbon) group.

19. The method of claim 1, wherein R$^{H3}$ is a monovalent saturated hydrocarbon group, a halogeno monovalent saturated hydrocarbon group, a hetero atom-containing monovalent saturated hydrocarbon group or a halogeno (hetero atom-containing monovalent saturated hydrocarbon) group.

20. The method of claim 1, wherein $R^{HB}$ is a monovalent saturated hydrocarbon group.

21. The method of claim 1, wherein $R^{HB}$ is a halogeno monovalent saturated hydrocarbon group.

22. The method of claim 1, wherein $R^{HB}$ is a hetero atom-containing monovalent saturated hydrocarbon group.

23. The method of claim 1, wherein $R^{HB}$ is a halogeno (hetero atom-containing monovalent saturated hydrocarbon) group.

24. The method of claim 1, wherein the reaction temperature for the fluorination reaction ranges from −50 to +100° C.

25. The method of claim 1, wherein the amount of fluorine gas used for the fluorination ranges from 5 to 30 vol. %.

* * * * *